(12) United States Patent
Haske

(10) Patent No.: US 7,315,356 B2
(45) Date of Patent: Jan. 1, 2008

(54) FIRE DEMONSTRATION TOOL AND METHOD FOR USING THEREOF

(76) Inventor: Martin D. Haske, 77 Pond Ave. C609, Brookline, MA (US) 02445

( * ) Notice: Subject to any disclaimer, the term of this patent is extended or adjusted under 35 U.S.C. 154(b) by 603 days.

(21) Appl. No.: 10/845,386

(22) Filed: May 13, 2004

(65) Prior Publication Data

US 2005/0254037 A1    Nov. 17, 2005

(51) Int. Cl.
*G01N 21/00* (2006.01)

(52) U.S. Cl. ...................................... 356/30

(58) Field of Classification Search ............... 356/30, 356/31; 382/123, 141, 149; 359/385, 798, 359/801, 804, 885
See application file for complete search history.

(56) References Cited

U.S. PATENT DOCUMENTS

| | | | |
|---|---|---|---|
| 1,744,485 A | 1/1930 | Michel et al. | |
| 2,494,078 A | 1/1950 | Woodruff | |
| 2,934,993 A | 5/1960 | Chromy | |
| 3,867,032 A | 2/1975 | Bruck | |
| 4,529,305 A | 7/1985 | Welford et al. | |
| 5,196,966 A | 3/1993 | Yamashita | |
| 5,260,763 A | 11/1993 | Yamashita | |
| 6,292,315 B1 | 9/2001 | Ravich et al. | |
| 6,473,164 B1 | 10/2002 | De Jong et al. | |

*Primary Examiner*—Hwa (Andrew) Lee
*Assistant Examiner*—Roy M. Punnoose

(57) ABSTRACT

The present invention is directed to a device for imaging a gem, and more specifically, a device capable of imaging the fire of a gem and thereby enabling the qualitative assessment of the fire of the gem. The gem imaging device of the present invention includes an exterior assembly and an inner assembly. The exterior assembly includes a viewing system, an outer housing and a base, while the inner assembly includes a view opening, a light baffle, an illumination mechanism, a diffuser plate mechanism, an outer chamber, an inner chamber, a perforated inner compartment and a rotation mechanism. In use, a user images a gem located in the inner assembly of the gem imaging device, and specifically, located within the inner chamber. Based on the light reflected on, into or from the gem, the user may image the gem, and specifically, the fire of the gem.

12 Claims, 4 Drawing Sheets
(1 of 4 Drawing Sheet(s) Filed in Color)

FIRE DEMONSTRATION TOOL AND METHOD FOR USING THEREOF

BACKGROUND OF INVENTION

1. Field of Invention

The present invention is directed to a device for imaging a gem, and more specifically, a device capable of imaging the fire of a gem and thereby enabling the qualitative assessment of the fire of the gem.

2. Description of the Related Art

For purposes of this invention, the term "gem" or "gems" will be used to describe gemstones, diamonds, minerals, rocks, petrified material, amber, manufactured gems, stone, and any other solid transparent or translucent material capable of refracting and dispersing light.

There are four commonly recognized quality factors of gems, and specifically, of diamonds. These four quality factors, commonly referred to as "color," "clarity," "carat," and "cut," were promoted by the DeBeers Diamond Company starting in 1948. Today, these four quality factors are used by both consumers and the gemological industry to appraise the value of a gem.

For example, the "color" of a diamond is usually rated on a color-grading scale, which ranges from D (colorless) to Z (light yellow). The color-grading scale is used by comparing a diamond with pre-graded comparison stones. For example, while colorless diamonds are widely considered the most rare and expensive, most jewelry diamonds are nearly colorless or have a faint touch of yellow.

"Clarity" relates to the flawlessness of a gem. Generally, for example, a diamond is categorized in six broad grading categories: (i) flawless, commonly referred to as "F", (ii) internally flawless, commonly referred to as "IF", (iii) very, very slightly included, commonly referred to as VVS1 and VVS2, (iv) very slightly included, commonly referred to as VS1 and VS2, (v) slightly included, commonly referred to as SI1 and SI2, or (vi) included, commonly referred to as either I1, I2, or I3. Categorizations are usually based on examination of gems with a binocular microscope at 10×. IF gems, are considered the most rare and the most expensive of all gems.

The term "carat" indicates the weight of a gem. A carat is equal to 200 milligrams and is divided into 100 points. Gems of one carat or more are generally considered more rare, and generally, the cost of the gem increases along with the carat weight.

The final quality factor is "cut." Cut refers not only to the shape of the gem, but also to its proportions, symmetry and polish. Some skilled in the art believe that the quality of the cut is primarily responsible for making a gem appear brilliant and colorful, or in the alternative, dull and lifeless.

The most widely used standards for grading the cut of a diamond are those of the American Gem Society (hereinafter referred to as the "AGS"). The AGS system rates a diamond's cut according to proportions, symmetry and polish. The AGS grading systems generally rank diamonds from zero (0) to ten (10), with zero (0) being the highest in each category. Diamonds that achieve zero scores in the proportions, symmetry and polish categories are commonly called "Triple Zeros" in the industry.

However, even an ideally cut gem can still fail what is often considered the most important element of gem beauty: maximum fire. Fire is defined as the colored rays of light arising due to the dispersion of light through a gem. A gem with maximum fire will reflect a significant amount of available light from the gem to a viewer's eye, thereby revealing the fire of all the colors in the spectrum. There are two common types of fire: broadflash or pinfire. The type of fire reflected to a viewer is determined by the viewer's overall ability to see the fire in a typically complex illumination environment. A gem is considered to exhibit broadflash fire when whole facets of the gem exhibit the same purer spectral hue. Broadflash fire is considered to be superior to pinfire fire, wherein a gem returns a constant color in much smaller areas. It is more difficult, if not impossible, for a viewer to resolve the fire of a gem when the constant color is located in a smaller area.

A purchaser of a gem is likely to be interested in assessing the four quality factors of a gem, as well as the fire of the gem. This assessment will preferably occur prior to the purchase of the gem. Thus, the gemological industry has created a number of instruments capable of assessing various quality attributes of a gem.

For example, U.S. Pat. No. 3,867,032 assigned to Diharo Diamanten Handels Compagnie Establishment, and entitled Arrangement for Objectively Evaluating Characteristics of Gems, Particularly Diamonds (the "'032 Patent"), discloses a device that is specifically designed to provide an arrangement for evaluating cut gems, especially diamonds. The '032 Patent discloses an arrangement wherein a diamond is located at the bottom of an ellipsoidal housing. The ellipsoidal housing has an interior surface, a portion of which is formed as an ellipsoidal mirror. Light emitted from the end of a fiber optic element into the top of the ellipsoidal housing is shown into the diamond. The brilliance of the diamond is measured by placing photocells both below the diamond and at the top of the ellipsoidal housing. According to the '032 Patent, an ideal diamond will reflect light out of the upper portion of the diamond. A less than ideal diamond will either absorb the light or allow it to pass through to the photocells located directly below the diamond.

Another example of a gem assessing device may be found in U.S. Pat. No. 5,196,966, assigned to Massayo Yamashita, entitled Method and Implement for Observing or Photographing Gems such as a Diamond (the "'966 Patent"). This implement is specifically designed to permit one to precisely know the degree of the brilliance of a diamond, the colors of the light, and so on. The implement, as disclosed in the '966 Patent, is generally comprised of a base with a cylindrical container set on top of the base. A diamond is placed inside the container. Located at the top of the container is a surface that has a hole through which a camera or other viewing device may be positioned in order to photograph or view the diamond. In use, either natural light or an illuminating device reflects light either: (a) directly into the container to the diamond; or (b) against the base, up against the surface and into the container to the diamond.

A further example of a gem assessing device may be found in U.S. Pat. No. 5,260,763, assigned to Massayo Yamashita, entitled Instrument for Observing Jewels' Brilliance as Diamond, and Method of Taking Photographs with Said Instrument (the "'763 Patent"). The instrument is specifically designed to observe the brilliance of jewels, especially of diamonds, and a method of photographing them with this instrument. Essentially, the instrument includes a tubular vessel comprised of elements such as a lower tubular portion that does not permit the passage of light (or alternatively, is chromatic as red) and an upper tubular portion which is semi-transparent. The semi-transparent nature of the upper tubular portion limits and makes uniform the light entering the tubular vessel and into a diamond. The upper tubular portion may be reshaped to adjust the entering light volume. Further, a black cloth may be placed between the upper tubular portion and lower tubular portion to lessen the light entering into the diamond.

While the devices set forth in the '032 Patent, '966 Patent, and '763 Patent assess certain attributes of a diamond, there is currently a need in the gemological industry for a device capable of capturing an image of the fire of a gem in a qualitatively repeatable manner.

BRIEF SUMMARY OF THE INVENTION

The present invention is directed to a device for imaging a gem, and more specifically, a device capable of imaging the fire of a gem and thereby enabling the qualitative assessment of the fire of the gem.

The gem imaging device of the present invention includes an exterior assembly and an inner assembly. The exterior assembly includes a viewing system, an outer housing and a base. In a preferred embodiment, the viewing system includes an image capturing device, a lens, and an optional polarizing filter.

The inner assembly includes a view opening, a light baffle, an illumination mechanism, a diffuser plate mechanism, an outer chamber, an inner chamber, an inner compartment, a rotation mechanism and a gem holder. In a preferred embodiment, the diffuser plate mechanism is comprised of a plurality of filters and a color correction plate.

In use, a gem is placed on the gem holder in the inner assembly of the gem imaging device. A user may then view the gem using the viewing system. Based on the light reflected on, into or from the gem, the user may image the gem, and specifically, the fire of the gem.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention is directed to a device 200 for imaging a gem 300, and more specifically, a device 200 capable of imaging the fire of a gem 300 and thereby enabling its qualitative assessment. The gem imaging device 200 of the present invention allows a user to image the fire of a gem 300 in a qualitatively repeatable manner.

For purposes of this detailed description, imaging a gem 300 in a qualitatively repeatable manner means that, while rotation or repositioning of the gem 300 may change the color of an individual fact of the gem 300, the overall quality of the characterization of the gem 300 is relatively unchanged.

Further, the term "imaging," as used throughout this detailed description, means viewing and capturing the image of a gem 300 by means of an eye, a camera, a video camera, telescope, or any other device capable of viewing, capturing, recording, or photographing a gem 300.

Figure 1:
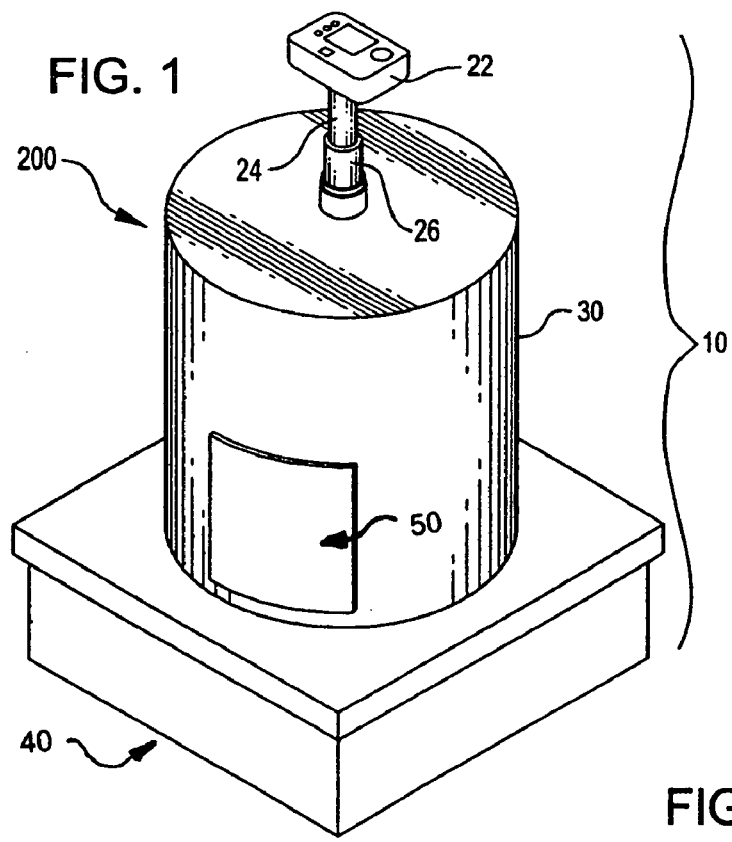
FIG. 1 is a drawing of a perspective exterior view of an improved gem imaging device of the present invention.
Figure 4:
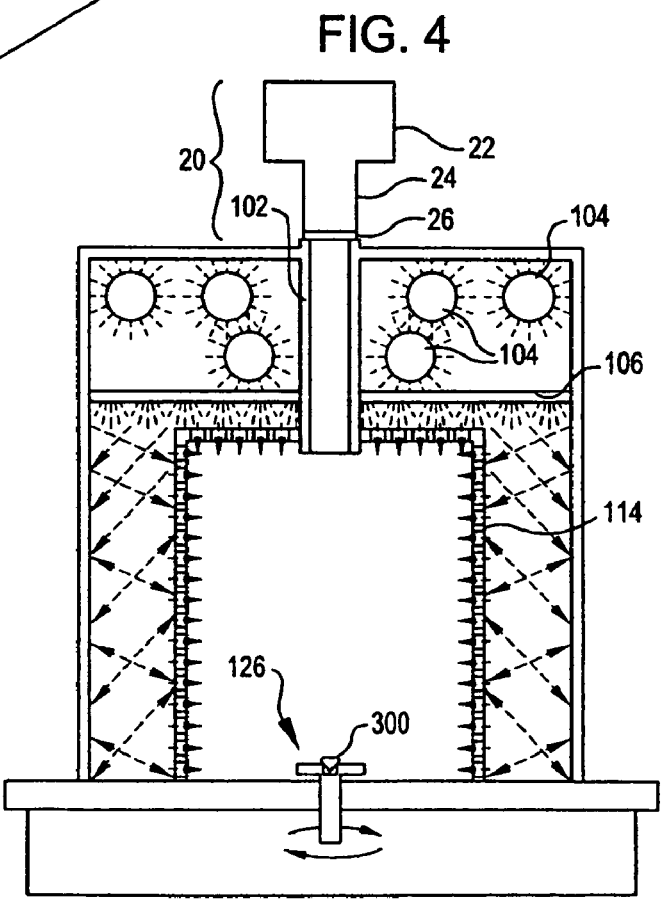
FIG. 4 is a drawing of a cross-sectional interior view of the exemplary embodiment of the gem imaging device.
Figure 2:
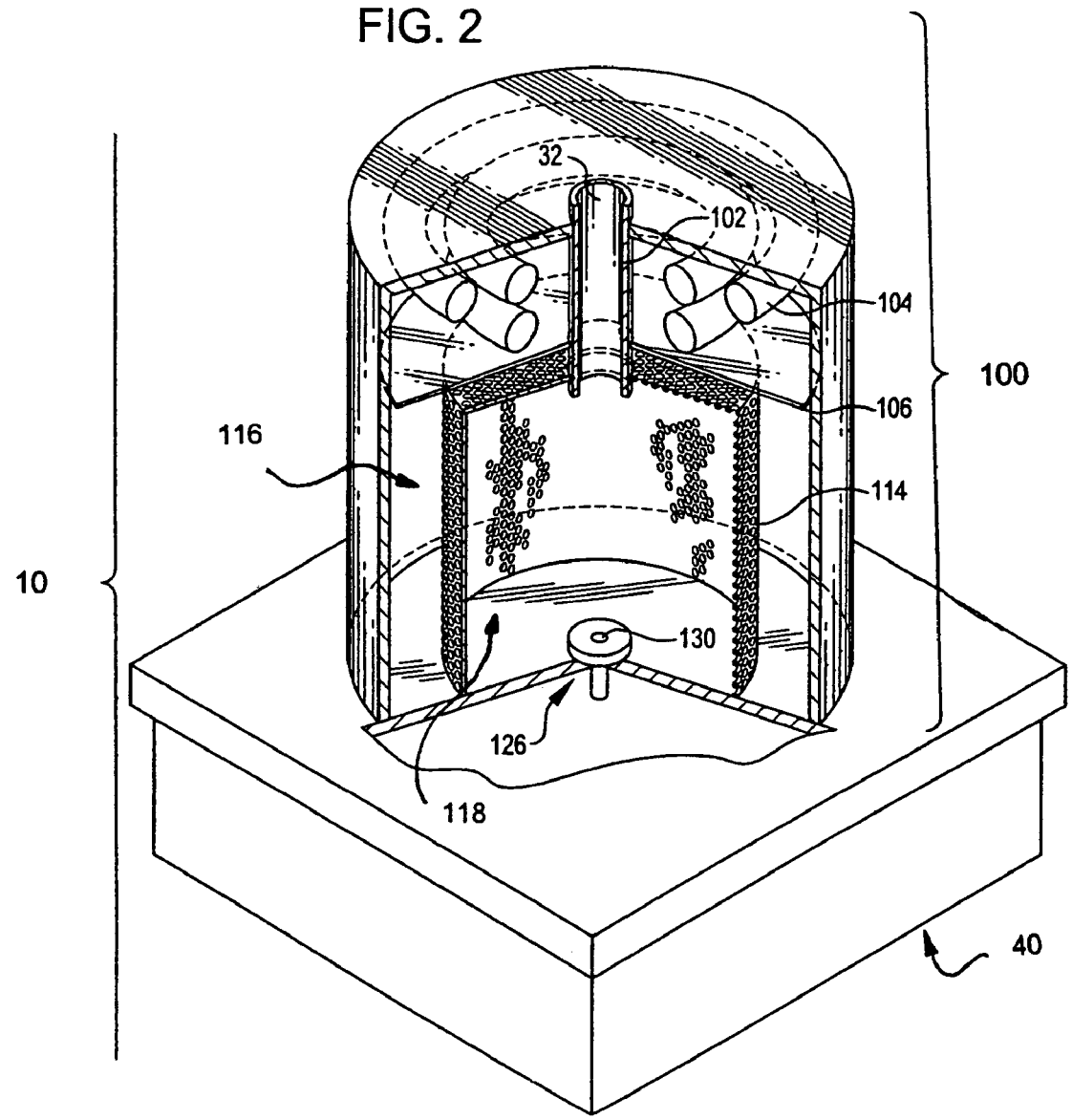
FIG. 2 is a drawing of an interior perspective view of the exemplary embodiment of the gem imaging device shown in FIG. 1.

The gem imaging device 200, as shown in FIGS. 1–4, includes an exterior assembly 10 and an inner assembly 100. The exterior assembly 10 of the gem imaging device 200 is shown in FIG. 1, while the inner assembly 100 of the gem imaging device 200 is shown in FIGS. 2 and 4.

A. Exterior Assembly

As shown in FIG. 1, the exterior assembly 10 of the gem imaging device 200 includes a viewing system 20 shown in (FIG. 4), an outer housing 30, and a base 40. The outer housing 30 houses the inner assembly 100 of the gem imaging device 200. As shown, the outer housing 30 may be cylindrical, but other shapes and geometries (e.g. spherical, square, rectangular) may be possible. As further discussed below, the base 40 at least partially houses a rotation mechanism 126 (shown in detail in FIG. 3), as well as necessary electronics, including fluorescent ballasts and lighting controls, that may be used in connection with the illumination mechanism 104.

The viewing system 20 is preferably located at the top of the outer housing 30. The viewing system 20 includes an image capturing device 22 (shown in FIG. 1 as a camera), a lens 24, and an optional polarizing filter 26. One of the purposes of the viewing system 20 is to provide a user with viewing accessibility into the inner assembly 100 of the gem imaging device 200.

In a first embodiment, the image capturing device 22 may simply be a user's eye (not shown). In a second, and preferred embodiment, the image capturing device 22 is a camera, telescope, video camera, or any other device capable of imaging a gem 300 located within the inner assembly 100 of the gem imaging device 200. For purposes of enablement, a third embodiment of the image capturing device 22 is a Nikon D1X digital camera. A digital camera or digitized images allows for the separate qualitative and quantitative analysis of the images of the gem 300. A qualitative and quantitative analysis of a gem 300 allows it to be compared with other gems 300 that have been imaged using the gem imaging device of the present invention 200.

Located below the image capturing device 22 is a lens 24. The lens 24 allows for the magnification of the interior of the gem imaging device 200. If a digital camera is used as the image capturing device 22, it is preferred that the digital camera be used in connection with a lens 24 such as a macro lens 24'. A macro lens 24' is a camera lens designed to focus at very short distances with up to life-size, or greater, magnification of an image. When used in connection with the gem imaging device 200, the macro lens 24' will optimally provide high-resolution images of the gem 300. If a macro lens 24' is used as part of the viewing system 20, it is preferred that the macro lens 24' be of 200 mm or higher, with a camera lens aperture setting smaller than f22.

In a further option, and as shown in FIGS. 1 and 4, an optional polarizing filter 26 may be located below the lens 24. The purpose of the optional polarizing filter 26 is to reduce the front surface glare from the gem 300 and improve the ability to image the refracted light from the gem 300. Either a linear or circular polarizing filter 26 may be used in connection with the viewing system 20.

B. Interior Portion

Preferably, and as shown in FIG. 4, the viewing system 20 is directed into a view opening 32 (referenced in FIG. 2) located at the top of the outer housing 30. The view opening 32 at the top of the outer housing 30 provides viewing access into the inner assembly 100 of the gem imaging device 200. The inner assembly 100 of the gem imaging device 200 includes a light baffle 102, illumination mechanism 104, diffuser plate mechanism 106, outer chamber 118, inner compartment 114, inner chamber 116, and rotation mechanism 126.

As shown in FIGS. 2 and 4, located below from the view opening 32 is preferably the light baffle 102. The light baffle 102 extends downward from view opening 32 down through the top of the inner compartment 114. A light baffle 102 is commonly known in the art, and is used to prevent extraneous source illumination light from interfering with the reflected light from the gem 300 being imaged using the gem imaging device 200 of the present invention.

Surrounding the exterior of the light baffle 102, is an illumination mechanism 104. As shown in FIG. 2, in a preferred embodiment, the illumination mechanism 104 is located at the top of the inner assembly 100, and is comprised of a plurality of lights or other sources of illumination. It should be noted that in a first alternate embodiment, the illumination mechanism 104 is located at bottom of the inner assembly 100. In a second alternate embodiment, the illumination mechanism 104 is located peripherally to the inner compartment 114. In a third alternate embodiment, the illumination mechanism is comprised of a plurality of lights located evenly and/or symmetrically throughout the inner assembly, and specifically, throughout the outer chamber 118 (discussed below).

In the shown embodiment of the illumination mechanism 104, the plurality of lights are fluorescent ring lights. The illumination mechanism 104 may be electronically dimmable or the illumination mechanism 104 may be fixed, ring light illuminators. It should be noted that incandescent illumination is an alternative type of illumination mechanism 104 that could be used in the present invention. Incandescent illumination, however, would require a different diffusing mechanism to assure uniformity and symmetry in illumination intensity. Color temperature adjusted incandescent lighting may also be used, but it may require a different and/or larger illumination mechanism assembly.

Preferably located below the illumination mechanism 104 is a diffuser plate mechanism 106. In one preferred embodiment, the diffuser plate mechanism 106 is comprised of a plurality of filters (not shown) and a color correction plate (not shown). The diffuser plate mechanism 106 preferably operates to filter out the ultraviolet component of the light exiting the illumination mechanism 104 from the inner assembly 100 of the gem imaging device 200. The diffuser plate mechanism 106 also preferably increases the color temperature of the incident white light above 6500 degrees Kelvin. It should be noted that the diffuser plate mechanism is trying to reproduce the color temperature of shaded daylight. It should also be noted that a higher color temperature is likely required in order to produce "white" light, which is believed to be more uniformly distributed in wavelengths, rather than the yellowish light of most incandescent lighting.

Individually, the color correction plate operates to diffuse and soften the light emanating from the illumination mechanism 104, while the plurality of filters assist in the elimination of ultraviolet light within the inner assembly 100 of the gem imaging device 200. The plurality of filters may be manufactured from glass, plastic resin, gelatin or any other material that eliminates the transmission of ultraviolet light from the illumination mechanism 104.

Distribution of light to the inner compartment 114 requires that the color temperature of the lighting not be altered during the process so as to prevent destruction of the corrected color temperature prior to entering the inner compartment 114. As such, it is preferred that the inner assembly 100 of the gem imaging device 200 and the exterior surface of the inner compartment 114 be coated with a diffuse reflecting material (not shown). The diffuse reflecting material assists in maintaining the color temperature of the light emanating from the illumination mechanism 104. The diffuse reflecting material may be an aluminized surface, other spectrally flat reflection media, as used in integrating spheres such as Barium Sulfate ($BaSO_4$), Magnesium Oxide (MgO) or DURAFLECT® or SPECTRAFLECT® (both owned by Labsphere, Inc., a New Hampshire corporation, P.O. Box 70, Shaker Street, North Sutton, N.H. 03260), or a spectrally flat white paint or silvered (aluminized) paint.

Preferably, defined between the inner surface of the outer housing 30 and the outer surface of the inner compartment 114 is an outer chamber 118. It should be noted that the diffuser plate mechanism 106 may further define and enclose the outer chamber 118. For example, in the shown embodiment of FIG. 2, the diffuser plate mechanism further defines and encloses the upper limits or ceiling of the outer chamber 118.

Located within the inner assembly 100 and below the diffuser plate mechanism 106 is an inner compartment 114. In a preferred embodiment, the inner compartment 114 is a hemisphere, although it is possible that the inner compartment 114 may be other shapes and geometries (e.g. spherical, square, rectangular). Preferably defined within the inner compartment 114 is an inner chamber 116.

As previously stated, the light baffle 102 extends downward into the top of the inner compartment 114. As shown in FIGS. 2 and 4, the inner compartment 114 is secured to the base 40. Preferably, the inner compartment 114 is removably secured to the bottom of the base 40.

As shown in FIGS. 2 and 4, the inner compartment 114 is perforated. The perforations on the inner compartment 114 allow light to enter the inner compartment 114 with a non-aliasing source of a plurality of quasi pinpoint illumination sources. This type of light is often called "dappled lighting." It should be noted that dappled lighting is preferred over a single source of light because the facets of the gem 300 upon which the single source of light impinges will be different when the gem 300 is rotated. This would likely result in radically different images of the gem 300. Dappled lighting is therefore a preferential lighting scheme because it allows a user to obtain repeatable images of a gem 300.

It is preferred that the interior surface of the inner compartment 114 be coated with a spectrally flat black non-reflective material such as flat-black Krylon paint or carbon doped SPECTRAFLECT®. A spectrally flat non-reflective material optimally eliminates color mixing in the image from secondary light reflections which may alias the image.

Figure 3:
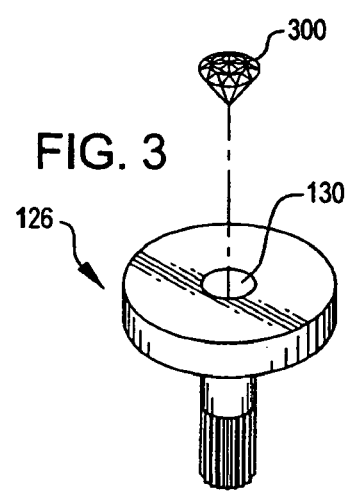
FIG. 3 is a drawing of a perspective view of an enlarged view of a rotation mechanism of the exemplary embodiment of a rotation mechanism of the gem imaging device.

Located in the inner chamber 116, and as shown in FIGS. 2 and 4, a rotation mechanism 126 extends from the base 40 into the inner assembly 100 of the inner compartment 114. The purpose of the rotation mechanism 126 is to allow the proper external positioning of a gem 300 to maximize the fire performance. The rotation mechanism 126 is a rotating platform which holds, and as shown in FIGS. 2–4, rotates the gem 300. Preferably, the rotation mechanism 126 is non-reflective. The rotation mechanism 126 may be manually rotated or, optionally, rotated using an automatic rotation apparatus. It should be noted that a non-rotatable embodiment could be produced in which the gem 300 must be manually repositioned. Further, it is also possible that other portions of the gem 300 could be rotated (e.g. the base 40, the inner compartment 114, the viewing system 20) instead of, or in addition to, the rotation mechanism 126.

Preferably located on, or as part of, the rotation mechanism 126 is a gem holder 130. Like the inside of the inner compartment 114, it is preferred, in a first preferred embodiment, that the gem holder 130 be covered with a spectrally flat non-reflective material such as carbon doped black SPECTRAFLECT®. In a second preferred embodiment, the gem holder 130 may be made of a spectrally flat reflective material like white SPECTRALON® (owned by Labsphere, Inc., a N.H. corporation, P.O. Box 70, Shaker Street, North Sutton, N.H. 03260) or similar product.

In use, as shown in FIG. 4, a gem 300 is preferably placed on the gem holder 130 of the rotation mechanism 126. In a first preferred embodiment, the gem 300 is placed on the gem holder 130 by opening a door 50 (shown in FIG. 1) located on the exterior assembly 10 of the gem imaging device 200 and placing the diamond 300 on the gem holder 130. In a second preferred embodiment, the gem 300 is placed on the gem holder 130 by lifting the inner compartment 114 and exterior assembly 10 of the gem imaging device 200, thereby providing access to the gem holder 130.

Figure 5:
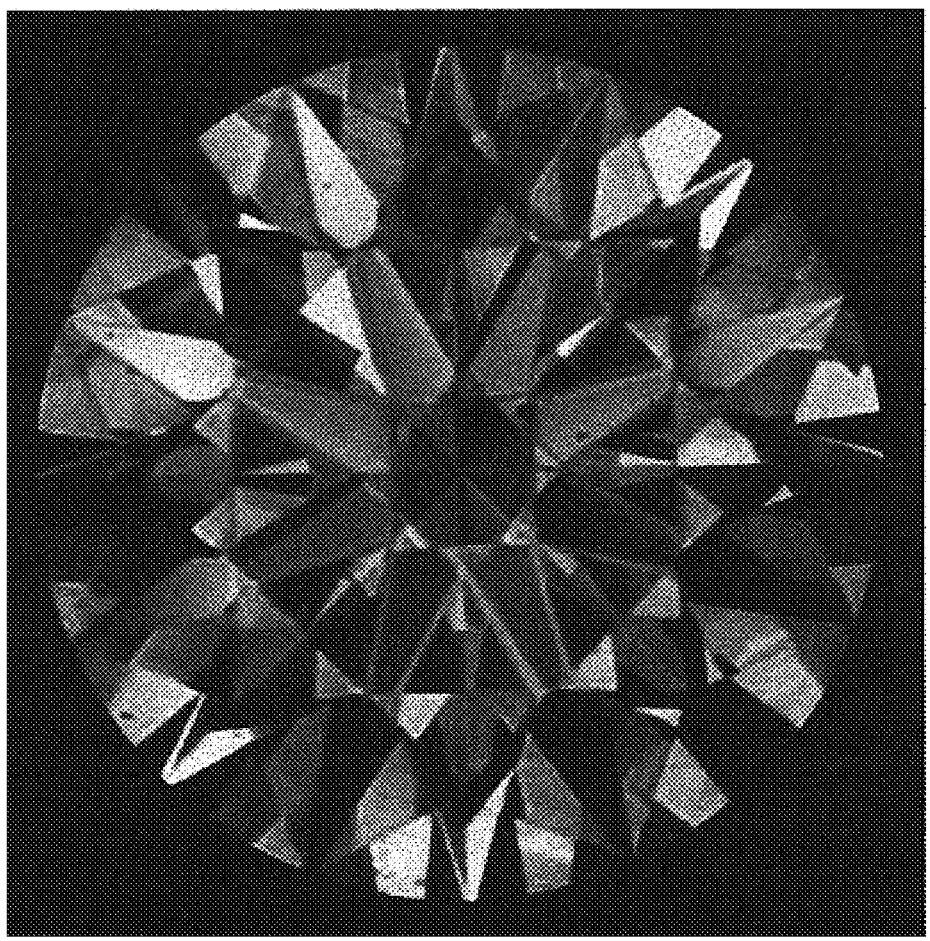
FIG. 5 is a black and white photograph of a gem taken by means of the gem imaging device.
Figure 6:
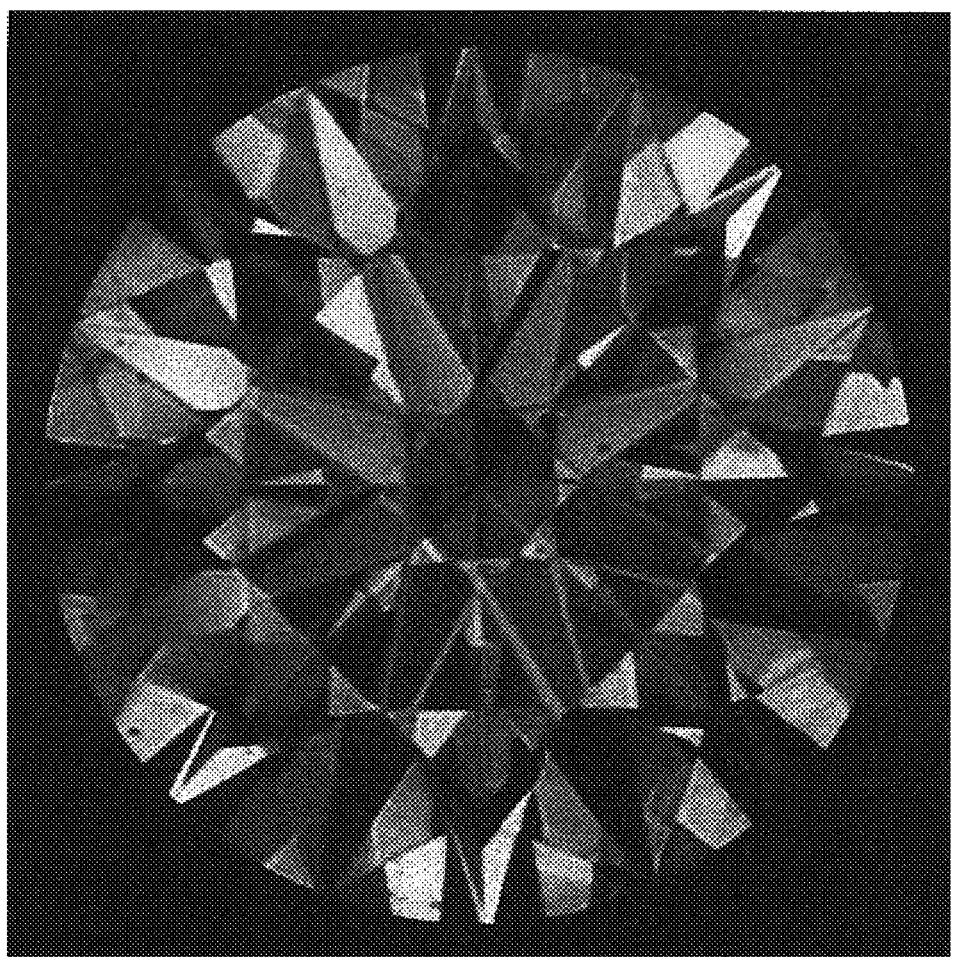
FIG. 6 is the original color photograph (saturation increased for printing) of the black and white photograph shown in FIG. 5.

The illumination mechanism 104 projects light, which in turn passes through the diffuser plate mechanism 106 and into the outer chamber 118, where it is diffusely reflected between the inner surface of the outer housing 30 and the outer surface of the inner compartment 114. The light is reflected towards and through the perforated inner compartment 114 into the inner chamber 116 as dappled light. The dappled light collides with the gem 300 that is preferably located on the rotation mechanism 126. The rotation mechanism 126 rotates the gem 300, and during the rotation process, the image capturing device 22 may image the refracted light as it exits the gem 300. FIG. 5 is a photograph of a gem 300 taken by means of the gem imaging device 200.

The terms and expressions used in the foregoing specification are used as terms of description and not of limitation, and are not intended to exclude equivalents of the features shown and described or portions of them. The scope of the invention is defined and limited only by the claims that follow.

What is claimed is:

1. A device for imaging a gem in a qualitatively repeatable manner, said device comprising:
   (a) an exterior assembly including an outer housing;
   (b) an inner assembly including a perforated inner compartment, said inner assembly positioned within said outer housing;
   (c) an illumination mechanism for providing light through said perforated inner compartment; and
   (d) wherein said device captures an image of refracted light exiting a gem positioned within said perforated inner compartment.

2. The device of claim 1, said exterior assembly further comprising:
   (a) a viewing system; and
   (b) a base, said base located below said outer housing.

3. The device of claim 2, said viewing system including a lens and an image capturing device, said image capturing device located above said lens and chosen from a group consisting of:
   (a) an eye;
   (b) a camera;
   (c) a telescope; and
   (d) a video camera.

4. The device of claim 3, said viewing system further comprising a polarizing filter, said polarizing filter located below said lens.

5. The device of claim 1, said inner assembly further comprising:
   (a) a view opening;
   (b) a light baffle extending downward from said view opening;
   (c) an illumination mechanism surrounding said light baffle;
   (d) a diffuser plate mechanism positioned below said illumination mechanism; and
   (e) a rotation mechanism positioned within said perforated interior compartment.

6. The gem imaging device of claim 5, said illumination mechanism comprised of a plurality of fluorescent ring lights.

7. The gem imaging device of claim 5, said diffuser plate mechanism comprised of a plurality of filters and a color correction plate.

8. The gem imaging device of claim 5, said rotation mechanism further including a gem holder.

9. A device for imaging a gem, said gem imaging device comprising:
   (a) an exterior assembly, said exterior assembly including
      a viewing system;
      an outer housing, said outer housing located below said viewing system;
      and a base, said base located below said outer housing; and
   (b) an inner assembly, said inner assembly including
      a view opening;
      a light baffle, said light baffle extending downward from said view opening;
      an illumination mechanism, said illumination mechanism surrounding said light baffle;
      a diffuser plate mechanism, said diffuser plate mechanism located below said illumination mechanism;
      an inner compartment, said inner compartment located below said diffuser plate mechanism; and
      a rotation mechanism, said rotation mechanism extending from a base of said inner assembly.

10. A method for imaging a gem in a qualitatively repeatable manner, said method comprising:
    (a) projecting a plurality of lights within an inner assembly of a gem imaging device;
    (b) reflecting said plurality of lights towards a perforated inner compartment and onto a gem located within; and
    (c) imaging said gem as said plurality of lights colliding with said gem.

11. A method for imaging a gem in a qualitatively repeatable manner, said method comprising:
    (a) providing a gem imaging device comprising:
       an exterior assembly, said exterior assembly including
          a viewing system;
          an outer housing;
          and a base; and
       an inner assembly, said inner assembly including
          a view opening;
          a light baffle, said light baffle extending downward from said view opening;
          an illumination mechanism, said illumination mechanism surrounding said light baffle;

a diffuser plate mechanism, said diffuser plate mechanism located below said illumination mechanism;

an inner compartment, said inner compartment located below the diffuser plate mechanism; and a rotation mechanism, said rotation mechanism extending from a base of said inner assembly.

(b) positioning a gem on said rotation mechanism; and (c) directing said viewing system towards said view opening so as to view or photograph said gem.

12. A gem imaging device for imaging a gem in a qualitatively repeatable manner, said gem imaging device comprising:

(a) an outer housing;

(b) an inner chamber defined within a perforated inner compartment, said perforated inner compartment positioned within said outer housing;

(c) an outer chamber at least partially peripherally defined between said outer housing and said perforated inner compartment;

(d) an illumination mechanism for providing light through said perforated inner compartment and into said inner chamber; and (e) wherein refracted light exiting a gem positioned within said inner chamber is imaged as fire.

* * * * *